United States Patent
Cawley

(10) Patent No.: US 11,819,588 B2
(45) Date of Patent: Nov. 21, 2023

(54) SYSTEM AND METHOD FOR ULTRA-CLOSE PROXIMITY IRRADIATION OF ROTATING BIOMASS

(71) Applicant: Kimtron, Inc., Oxford, CT (US)

(72) Inventor: Peter Cawley, Bethlehem, CT (US)

(73) Assignee: KIMTRON, INC., Oxford, CT (US)

( * ) Notice: Subject to any disclaimer, the term of this patent is extended or adjusted under 35 U.S.C. 154(b) by 0 days.

(21) Appl. No.: 18/171,419

(22) Filed: Feb. 20, 2023

(65) Prior Publication Data

US 2023/0201400 A1   Jun. 29, 2023

Related U.S. Application Data

(63) Continuation of application No. 17/847,647, filed on Jun. 23, 2022, now Pat. No. 11,583,602.

(60) Provisional application No. 63/304,688, filed on Jan. 30, 2022, provisional application No. 63/214,247, filed on Jun. 23, 2021.

(51) Int. Cl.
  *A61L 2/26* (2006.01)
  *A61L 2/08* (2006.01)
  *A61B 6/00* (2006.01)

(52) U.S. Cl.
  CPC .............. *A61L 2/26* (2013.01); *A61B 6/4423* (2013.01); *A61L 2/082* (2013.01); *A61L 2202/11* (2013.01); *A61L 2202/122* (2013.01)

(58) Field of Classification Search
  CPC ........ A61L 2/26; A61L 2/082; A61L 2202/11; A61L 2202/122; A61B 6/4423
  See application file for complete search history.

(56) References Cited

U.S. PATENT DOCUMENTS

| 6,075,837 A  * | 6/2000 | Roos ................. A61B 6/4233 378/98.2 |
| 6,212,255 B1 | 4/2001 | Kirk |
| 6,389,099 B1 | 5/2002 | Gueorguiev |
| 6,614,876 B1 | 9/2003 | Kirk |
| 6,785,360 B1 * | 8/2004 | Annis ................. A61B 6/032 378/57 |

(Continued)

FOREIGN PATENT DOCUMENTS

| CA | 2976004 C | 8/2016 |
| CN | 101310773 A | 11/2008 |

(Continued)

OTHER PUBLICATIONS

Rad Source, "RS 420 Series Cannabis Decontamination Systems" Brochure, Feb. 2022 (4 pages).

(Continued)

*Primary Examiner* — Regina M Yoo
(74) *Attorney, Agent, or Firm* — Ware, Fressola, Maguire & Barber LLP

(57) ABSTRACT

An irradiation system is provided which comprises a cabinet housing one or more X-ray tubes providing an irradiation source for a biomass contained within a cylindrical container arranged on a rotating device. The X-ray tubes generate directional X-ray beams and are provided in ultra-close proximity to the container, and the X-ray tubes can be configured to traverse the container. The rotational movement and traversal during the irradiation process ensure a more even irradiation of the entire biomass in the container.

23 Claims, 9 Drawing Sheets

(56) References Cited

U.S. PATENT DOCUMENTS

| | | | |
|---|---|---|---|
| 6,928,315 B1* | 8/2005 | Nachaliel | A61B 5/0536 |
| | | | 600/407 |
| 7,515,686 B2 | 4/2009 | Kirk | |
| 8,000,436 B2 | 8/2011 | Seppi et al. | |
| 8,236,599 B2 | 8/2012 | Chang et al. | |
| 8,900,841 B2 | 12/2014 | Medoff et al. | |
| 9,818,569 B2 | 11/2017 | Ausburn | |
| 9,969,512 B2 | 5/2018 | Eidebakken et al. | |
| 10,080,276 B2 | 9/2018 | Hartman et al. | |
| 10,549,125 B2 | 2/2020 | Bergfjord et al. | |
| 2002/0107650 A1 | 8/2002 | Wack et al. | |
| 2004/0109532 A1 | 6/2004 | Ford et al. | |
| 2006/0023835 A1 | 2/2006 | Seppi | |
| 2007/0025515 A1 | 2/2007 | Kirk et al. | |
| 2008/0240362 A1* | 10/2008 | Yu | A61B 6/4476 |
| | | | 378/196 |
| 2010/0034346 A1* | 2/2010 | Kato | A61B 6/587 |
| | | | 378/115 |
| 2016/0278724 A1 | 9/2016 | Papaioannou | |
| 2018/0047540 A1 | 2/2018 | Ausburn | |
| 2019/0224712 A1 | 7/2019 | Petisce et al. | |
| 2019/0357868 A1 | 11/2019 | Bailey et al. | |
| 2021/0025796 A1 | 1/2021 | Czerniawski et al. | |
| 2021/0041378 A1* | 2/2021 | Morton | G01N 23/10 |

FOREIGN PATENT DOCUMENTS

| | | | | |
|---|---|---|---|---|
| CN | 102824698 A | 12/2012 | | |
| CN | 103889139 B | 6/2016 | | |
| CN | 105920746 A | 9/2016 | | |
| CN | 107743474 A | 2/2018 | | |
| CN | 109540939 A | 3/2019 | | |
| CN | 110201314 B | 9/2019 | | |
| CN | 209486011 U | 10/2019 | | |
| EP | 1129727 B1 | 1/2004 | | |
| EP | 2509963 B1 | 11/2015 | | |
| JP | 2004-67233 A | 3/2004 | | |
| JP | 2007-29709 A | 2/2007 | | |
| JP | 2018-138301 A | 9/2018 | | |
| JP | 6501822 B2 | 4/2019 | | |
| WO | 2014036056 A1 | 3/2014 | | |
| WO | 2014095839 A1 | 6/2014 | | |
| WO | 2014131173 A1 | 9/2014 | | |
| WO | 2014210425 A1 | 12/2014 | | |
| WO | WO-2017181214 A1 * | 10/2017 | | A22B 5/00 |
| WO | 2014145964 A1 | 9/2018 | | |
| WO | WO-2021030321 A1 * | 2/2021 | | G01N 23/046 |

OTHER PUBLICATIONS

International Search Report and Written Opinion, PCT/US22/34698, dated Oct. 11, 2022 (12 pages).

* cited by examiner

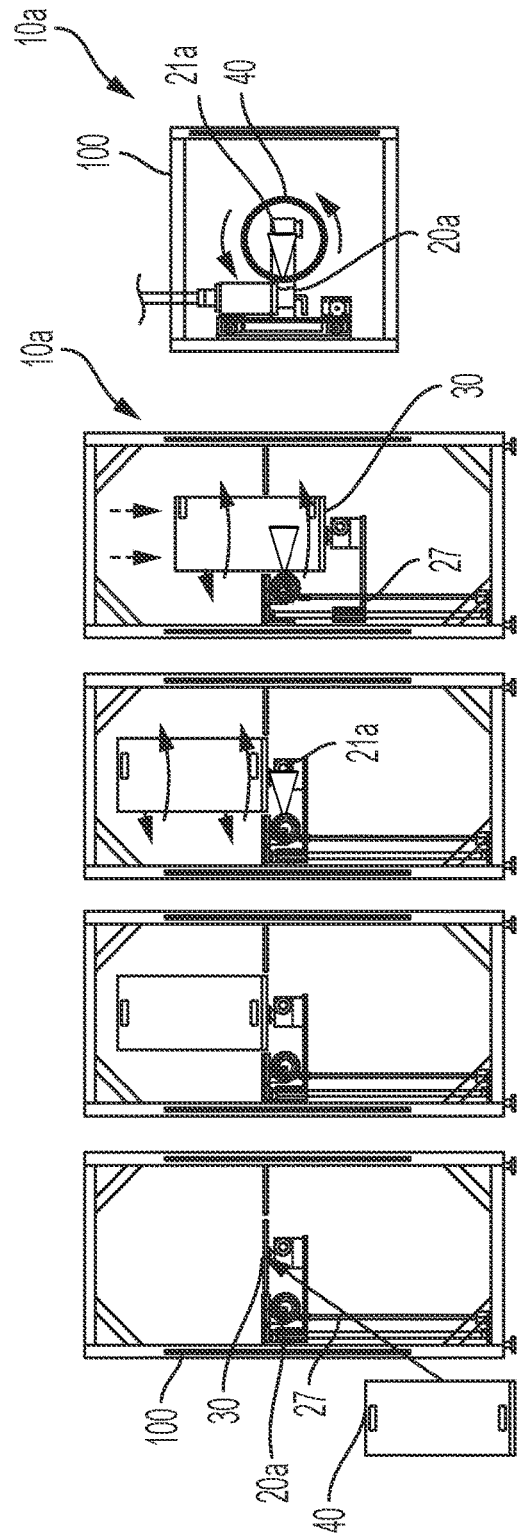

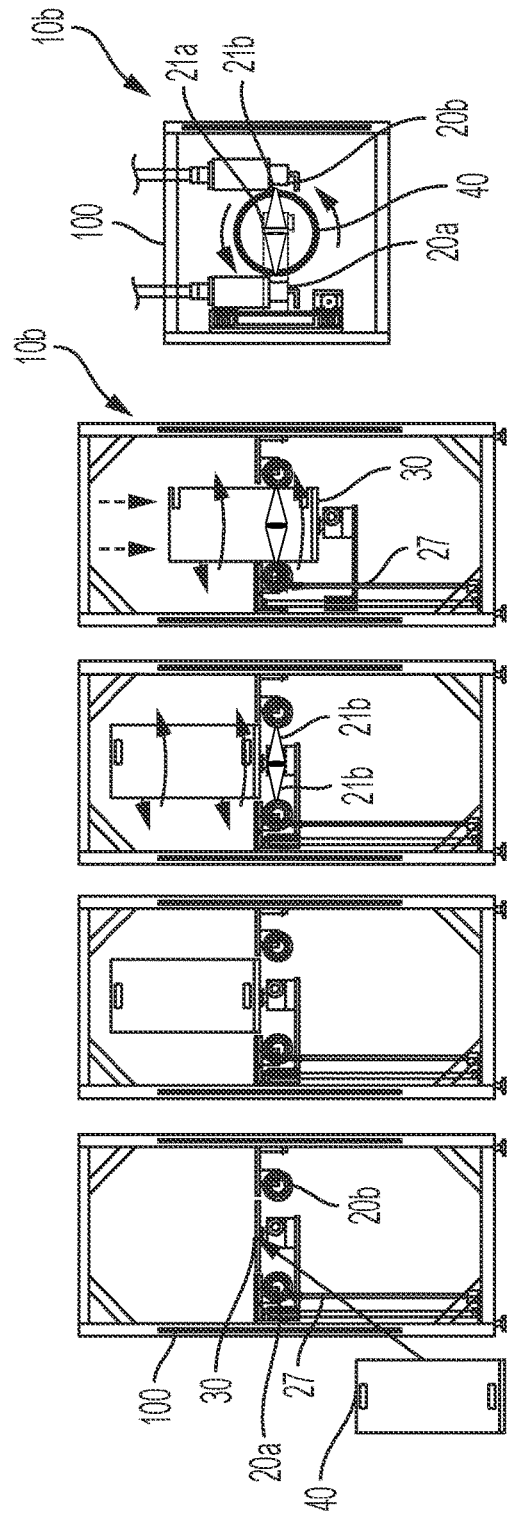
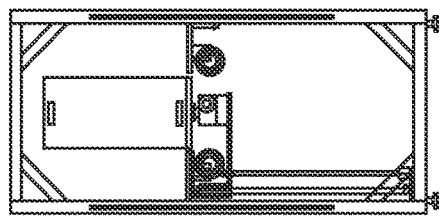
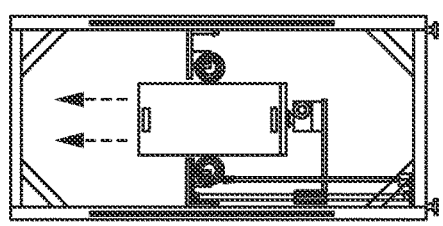
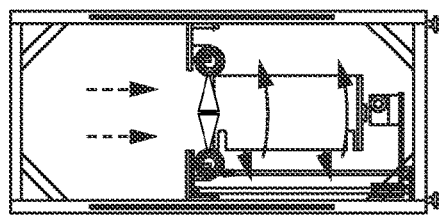
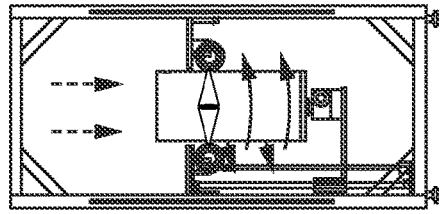

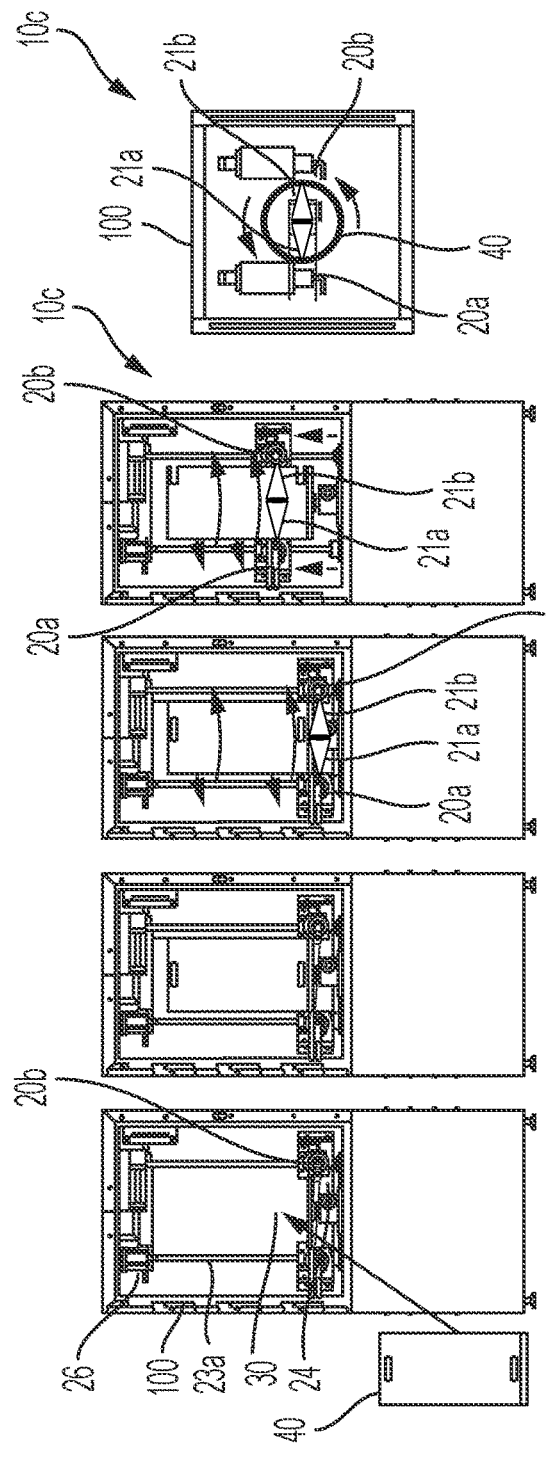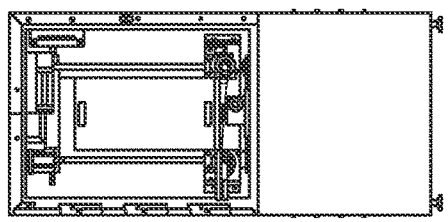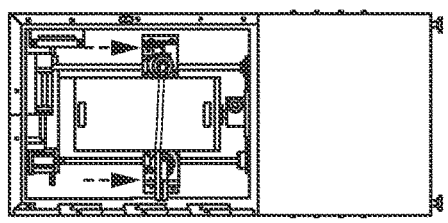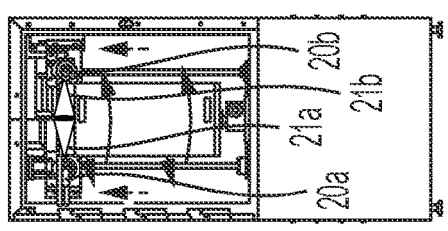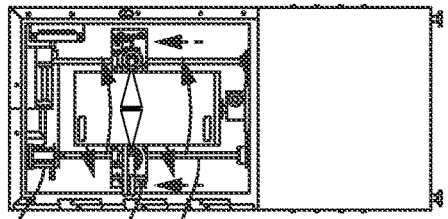

SYSTEM AND METHOD FOR ULTRA-CLOSE PROXIMITY IRRADIATION OF ROTATING BIOMASS

CROSS-REFERENCE TO RELATED APPLICATIONS

The present application is a continuation of U.S. patent application Ser. No. 17/847,647 filed Jun. 23, 2022, which claims the benefit of U.S. Provisional Application No. 63/214,247 filed Jun. 23, 2021 and U.S. Provisional Application No. 63/304,688 filed Jan. 30, 2022, which are each herein incorporated by reference in their entireties.

BACKGROUND OF THE DISCLOSURE

The present application relates to a method and a system for irradiating molds and other microbes from a biomass, such as *cannabis*, using ionizing irradiation (e.g., x-ray energy).

There are presently available different types of systems and devices for mold and microbial irradiation, which have several shortcomings. For example, some systems may include one or more stationary radiation generating devices within a cabinet. However, given the attenuation of the radiation over distance, these systems can provide an uneven radiation throughout the biomass, with the parts of the biomass furthest from the radiation generating device getting considerably less radiation dose, resulting in less than complete microbial irradiation and the parts of the biomass closest to the source being possibly damaged from over irradiation. Moreover, this process can take an extended period of time—five to nine hours. For example, if an X-ray tube is arranged at the bottom of a biomass, the bottom of the biomass will receive more radiation than the rest of the biomass. This results in either, or both of, an under-irradiation of the sections the container resulting in higher microbe and mold levels than permissible, or an excessive amount of energy having to be used over-irradiating the bottom of the biomass to overcompensate for the uneven irradiation of the biomass. Irradiators that utilize hemispheric or panoramic beam patterns may similarly result in an excess amount of energy use from directing radiation into empty space in a cabinet. Such systems may also position the radiation generating device(s) at a distance from the biomass, resulting in less of the radiation being received directly by the biomass, also reducing the effectiveness of the irradiation while increasing the amount of time required for the process. In other systems, a conveyor belt-type approach may be provided, where the biomass is conveyed along a moving surface adjacent to a radiation generating device. These systems suffer from similar shortcomings of the biomass being irradiated unevenly, and in the case of e-beam irradiation, are very costly and outside the financial reach of smaller growers and producers.

SUMMARY OF THE DISCLOSURE

In accordance with the present application, an irradiation system is provided which comprises a cabinet housing one, or a plurality of, X-ray tubes providing an irradiation source for a biomass contained within a cylindrical container arranged on a rotating device. The X-ray tubes are provided in ultra-close proximity to the container, with the conical beam of energy not necessarily encompassing the entire width of the container, and the X-ray tubes can be configured to traverse the container either vertically or horizontally depending on the orientation of the container—upright or laying horizontally. Coupled with the rotation of the container on the platform, the X-ray tube(s), which also traverse the length of the container during the irradiation process, ensure a more even irradiation of the entire biomass, from top to bottom and from the perimeter to the center.

In certain embodiments, the x-ray tube(s) may not necessarily traverse in unison but may make a single pass, make multiple passes, traverse in unison, or traverse in opposite linear directions. In some embodiments, the x-ray tubes may be stationary and the container itself is put in linear motion, either horizontally or vertically. The rotating biomass container may also be oriented on either the vertical or horizontal planes.

A bagged biomass is placed in a cylindrical container and "nested" on a rotating device in a cabinet or other enclosure via an access door. Upon initiating the start of the cycle, the container begins to rotate, and the x-ray tubes begin a slow, linear traverse along the axis of the biomass container, or the x-ray tube(s) will remain stationary as the rotating canister filled with biomass is raised and lowered.

The system of the present application provides greater homogeneity of dosage by rotating the biomass container. Rotation of the cylindrical canister ensures the outer portion of the biomass, which receives the most intense radiation dose, is exposed to the conical beam path(s) for less time than the center, which is constantly being dosed (irradiated). Therefore, as opposed to the center of biomass receiving only 25% of the dose that the perimeter of the biomass sees—as it would were the biomass container not under rotation—it receives just 50% less. Ionizing x-ray energy follows the inverse square law of light, mathematically expressed as $I \propto (1/d^2)$, and so the material closest to the source receives a much higher dose of radiation while the center of the canister receives much less. For example, doubling the distance from the source (e.g., point A) to subject (e.g., point B) will not halve the energy at point B, but will reduce that energy to one-fourth the energy at point A.

Using a plurality of x-ray tubes as described herein hastens the irradiation process proportionately—i.e., two x-ray tubes will process biomass twice as fast as one and four x-ray tubes will process biomass twice as fast as two.

The system of the present application also utilizes traversing x-ray tubes, or stationary x-ray tubes with a traversing biomass container, to ensure even dosage through the entire canister of biomass. Directional x-ray tubes do not generate a "flat" field of energy within the conical shaped beam pattern. Factors such as "heel effect" and a characteristically bell-shaped dose intensity curve across the field of view would make for inconsistent dosing throughout a static container. By traversing the energy parallel to the axis of rotation of the container, the dose results are extremely homogeneous and consistent (flat) along that plane. Because the perimeter of the rotating biomass is exposed to the most intense portion of the energy beam(s) only for a short period of time, and the center of biomass is exposed to the less intense portion of the energy beam(s) constantly, near homogeneity of dose is achieved laterally (across the diameter of the container). Because the energy beam(s) move linearly relative to a rotating container of biomass, absolute homogeneity of dose is achieved throughout the entire length of the container, parallel to its axis.

Varying the linear speed of the x-ray tube traverse at the leading edge of the canister further achieves even dose distribution throughout the canister. When the x-ray tube(s) begin the traverse below the bottom of the biomass container, the bottommost portion of material does not receive the same amount of radiation as the rest of the container due to the conical shaped beam. Therefore, the x-ray tubes can traverse more slowly at the leading edge (bottom) of the container to ensure sufficient dosage.

In accordance with a first aspect of the present application an apparatus is provided comprising an enclosure. The enclosure may include therein: a platform configured for axial rotation, and at least one x-ray tube configured to generate an x-ray beam directed in a first direction towards the platform, where either or both of the platform or the at least one x-ray tube are configured for movement within the enclosure in a second direction perpendicular to the first direction concurrent with the axial rotation of the platform.

Implementations of the apparatus of the first aspect of the present application may include one or more of the following features. In various embodiments of the apparatus, the at least one x-ray tube may include two x-ray tubes, each configured to generate x-ray beams and disposed opposite each other within the enclosure, such that one of the x-ray tubes generates an x-ray beam in the first direction and another of the x-ray tubes directed in a direction opposite the first direction. The two x-ray tubes are each configured for movement in the second direction concurrent with the axial rotation of the platform. The apparatus may further comprise: a support beam to which each of the two x-ray tubes is mounted; and a linear drive connected to the support beam configured to drive movement of the support beam and the two x-ray tubes. The two x-ray tubes may each also be configured for further movement in a third direction that is opposite the second direction, concurrent with the axial rotation of the platform.

In additional or alternative embodiments, the at least one x-ray tube may include two x-ray tubes, each configured to generate x-ray beams and disposed opposite each other within the enclosure, such that one of the x-ray tubes generates an x-ray beam in the first direction and another of the x-ray tubes directed in a direction opposite the first direction; and the platform may also be configured for further movement in a third direction that is opposite the second direction, concurrent with the axial rotation of the platform. The platform is configured for movement in the second direction concurrent with the axial rotation of the platform.

In additional or alternative embodiments, the at least one x-ray tube is configured for movement in the second direction concurrent with the axial rotation of the platform. The at least one x-ray tube may also be configured for further movement in a third direction that is opposite the second direction, concurrent with the axial rotation of the platform.

In additional or alternative embodiments, the at least one x-ray tube is configured for movement in the second direction concurrent with the axial rotation of the platform, and the platform is configured for movement in the second direction concurrent with the axial rotation of the platform. The platform may be configured for further movement in a third direction that is opposite the second direction, concurrent with the axial rotation of the platform. The apparatus may include a lifting system to which the platform is mounted, and which is configured to move the platform in the second and third directions concurrent with the axial rotation of the platform. The enclosure is a leaded cabinet. The platform can be configured to rotate 360°. The apparatus may also include a mount configured to mount the platform to a surface within the enclosure.

In accordance with a second aspect of the present application, a system is provided comprising an apparatus. The apparatus may comprise: an enclosure, including therein: a platform configured for axial rotation, and at least one x-ray tube configured to generate an x-ray beam directed in a first direction towards the platform, where either or both of the platform or the at least one x-ray tube are configured for movement within the enclosure in a second direction perpendicular to the first direction concurrent with the axial rotation of the platform. The system also includes a container disposed on the platform configured to hold contents to be irradiated by the at least one x-ray tube, where the platform is further configured to rotate the container disposed thereon.

Implementations of the system of the second aspect of the present application may include one or more of the following features. The container of the system can be placed in near surface contact or ultra-close proximity with the at least one x-ray tube, and the at least one X-ray tube emits a directional beam of energy, which beam does not encompass the entire container of biomass all at once. In various embodiments, the container is cylindrical, and at least a portion of a central axis of the container is exposed to the x-ray beam generated by the at least one x-ray tube and points on a perimeter of the container are intermittently exposed to the x-ray beam generated by the at least one x-ray tube.

In embodiments of the second aspect of the present application, the at least one x-ray tube may include two x-ray tubes, each configured to generate x-ray beams and disposed opposite each other within the enclosure so as to generate x-ray beams contacting opposite sides of the container. The two x-ray tubes can each be configured for movement in the second direction concurrent with the axial rotation of the platform. The two x-ray tubes may also each be configured for further movement in a third direction that is opposite the second direction, concurrent with the axial rotation of the platform. The two x-ray tubes are configured to traverse substantially an entire length of the container in the second direction and/or the third direction.

In additional or alternative embodiments of the second aspect of the present application, the at least one x-ray tube may include two x-ray tubes, each configured to generate x-ray beams and disposed opposite each other within the enclosure so as to generate x-ray beams contacting opposite sides of the container, and the platform is configured for movement in the second direction concurrent with the axial rotation of the platform. The platform is configured for further movement in a third direction that is opposite the second direction, concurrent with the axial rotation of the platform. The platform is configured to travel a distance in the second direction and/or in the third direction so as to expose substantially an entire length of the container to the x-ray beams generated by the two x-ray tubes.

In additional or alternative embodiments, the at least one x-ray tube is configured for movement in the second direction concurrent with the axial rotation of the platform; the at least one x-ray tube is configured for further movement in a third direction that is opposite the second direction, concurrent with the axial rotation of the platform; and the at least one x-ray tube can traverse substantially an entire length of the container in the second direction and/or the third direction.

In additional or alternative embodiments, the platform is configured for movement in the second direction concurrent with the axial rotation of the platform; the platform is configured for further movement in a third direction that is opposite the second direction, concurrent with the axial rotation of the platform; and the platform is configured to travel a distance in the second direction and/or the third direction so as to expose substantially an entire length of the container to the x-ray beam generated by the at least one x-ray tube.

In additional or alternative embodiments, the system may further comprise a temperature probe inside the enclosure configured to monitor a temperature inside the enclosure; and a cooling unit inside the enclosure configured to be switched on the temperature inside the enclosure reaches an upper temperature threshold.

In accordance with a third aspect of the present application, a method is provided. The method comprises loading a container stored with contents to be irradiated onto a platform in an irradiation apparatus and performing an irradiation process configured to irradiate the contents of the container. The platform is configured for axial rotation; and at least one x-ray tube of the irradiation apparatus is configured to generate an x-ray beam in a first direction towards the platform and the container. The irradiation process comprises concurrently: rotating the container on the platform, generating the x-ray beam by the at least one x-ray tube and directed the x-ray beam towards the container, and moving the platform or the at least one x-ray tube in a second direction perpendicular to the first direction concurrent with the axial rotation of the platform so that over the irradiation process, substantially an entire length of the container is exposed to the x-ray beam.

BRIEF DESCRIPTION OF THE FIGURES

FIGS. 5A-5I show an irradiation system according to the present application including a single, fixed X-ray tube.

FIGS. 6A-6I show an irradiation system according to the present application including two, fixed X-ray tubes.

FIGS. 7A-7I show an irradiation system according to the present application including two, moving X-ray tubes.

DETAILED DESCRIPTION OF THE FIGURES

Figure 1A:
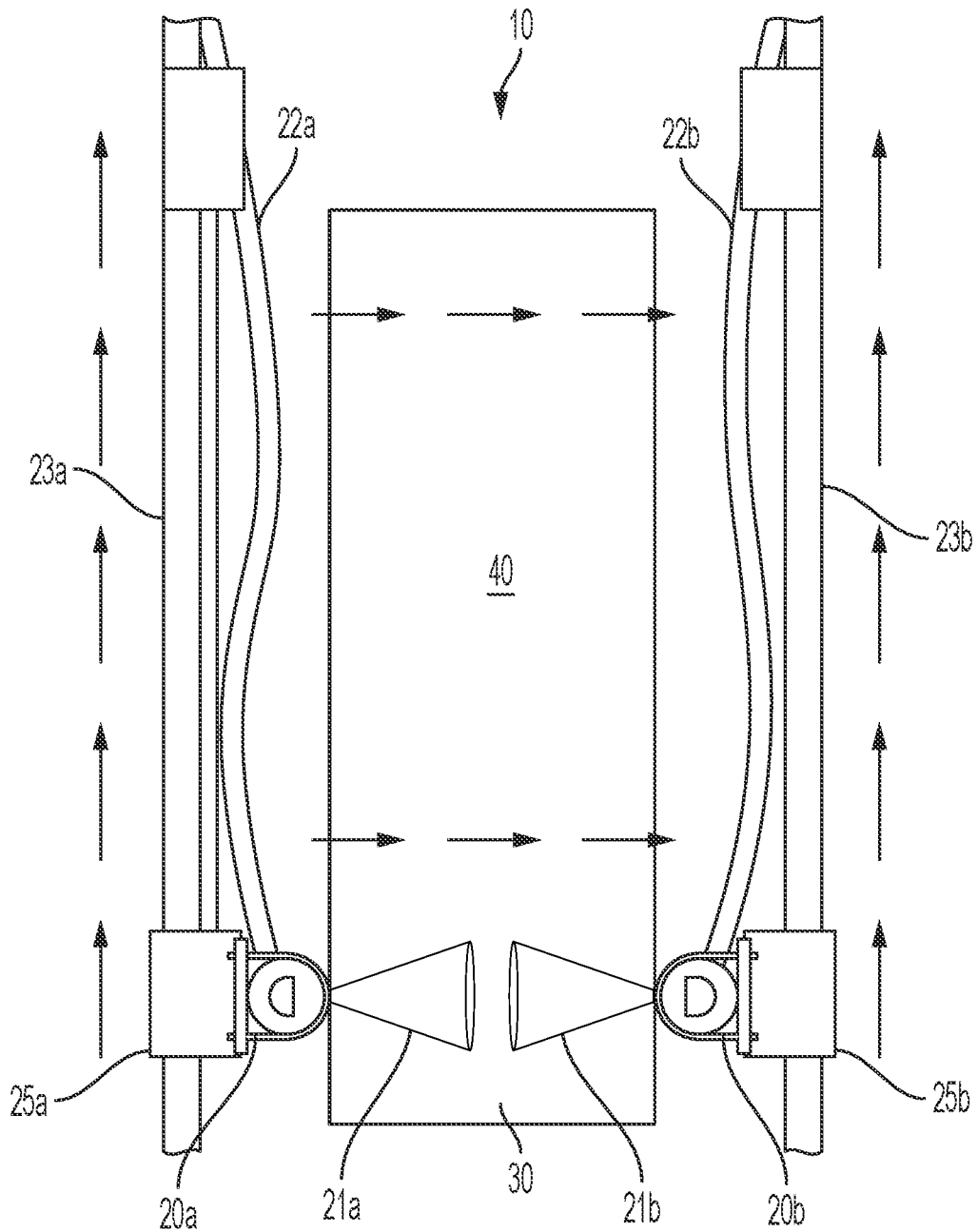
FIG. 1A shows a side view of an irradiation system according to an embodiment of the present application.

The irradiation system of the present application will be described with reference made to FIGS. 1A-7.

An irradiation system 10 is provided, which in particular embodiments, can be used for irradiation of mold and/or microbes on a biomass. In certain embodiments, the biomass may be plants such as *cannabis* plants, but the irradiation system 10 is not limited to use with irradiation of a particular subject or biomass and can be used in connection with other subject matter or biomass products that require remediation during their processing.

The irradiation system 10 comprises or can be contained in an X-ray cabinet 100 that is generally known in the art. The irradiation system 10 comprises a collection of components that are housed inside of an area of the cabinet 100 that can be accessed by way of an access door 101. In one embodiment, the irradiation system 10 comprises a pair of X-ray tubes 20a, 20b configured to generate conical X-ray beams 21a, 21b that are directed towards a container 40 arranged on a platform 30 within the cabinet 100. One or more power cables 22a, 22b are provided to supply power to the X-ray tubes for generating the X-ray beams 21a, 21b.

The platform 30 is configured for a rotational movement. As shown for example in FIGS. 3A-4B, a mount 31 can be provided to mount the platform 30 to the cabinet 100, and a rotational device comprising a connection 32 for receiving a motor 33 is provided, which enables the platform 30 to rotate 360°. The rotational speed of the platform can range from three to ten RPM. When the container 40 is placed on the platform 30 and the system 10 is in use, the container 40 and the biomass 41 arranged therein also rotate axially.

Figure 1B:
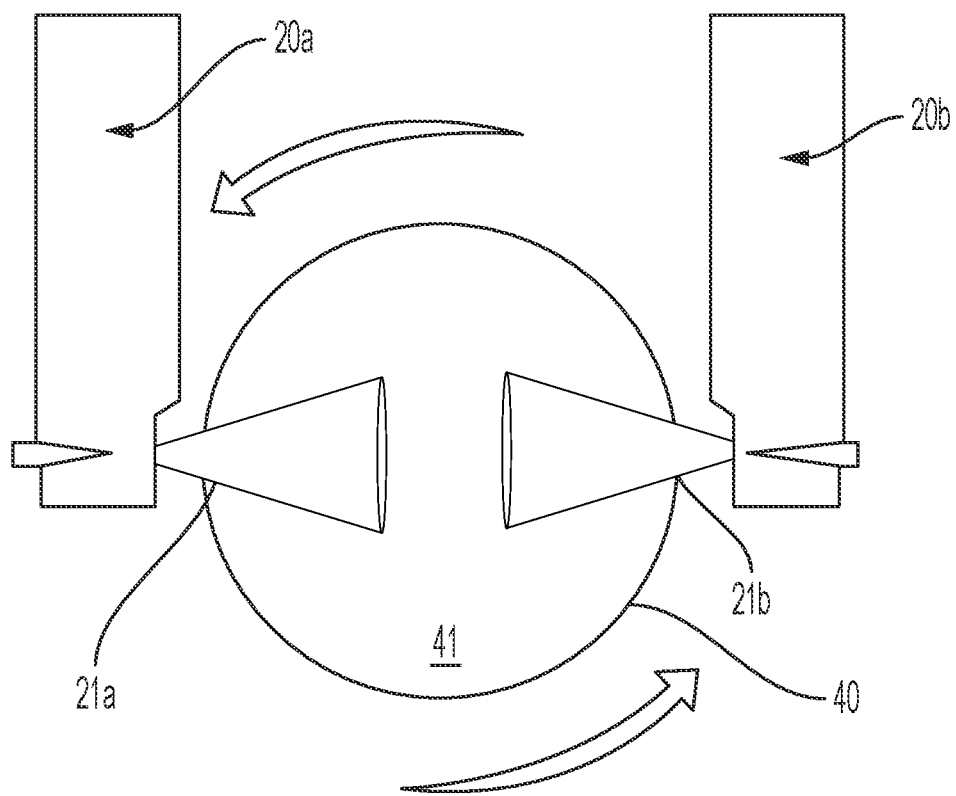
FIG. 1B shows a top view of the irradiation system according to an embodiment of the present application.
Figure 2:
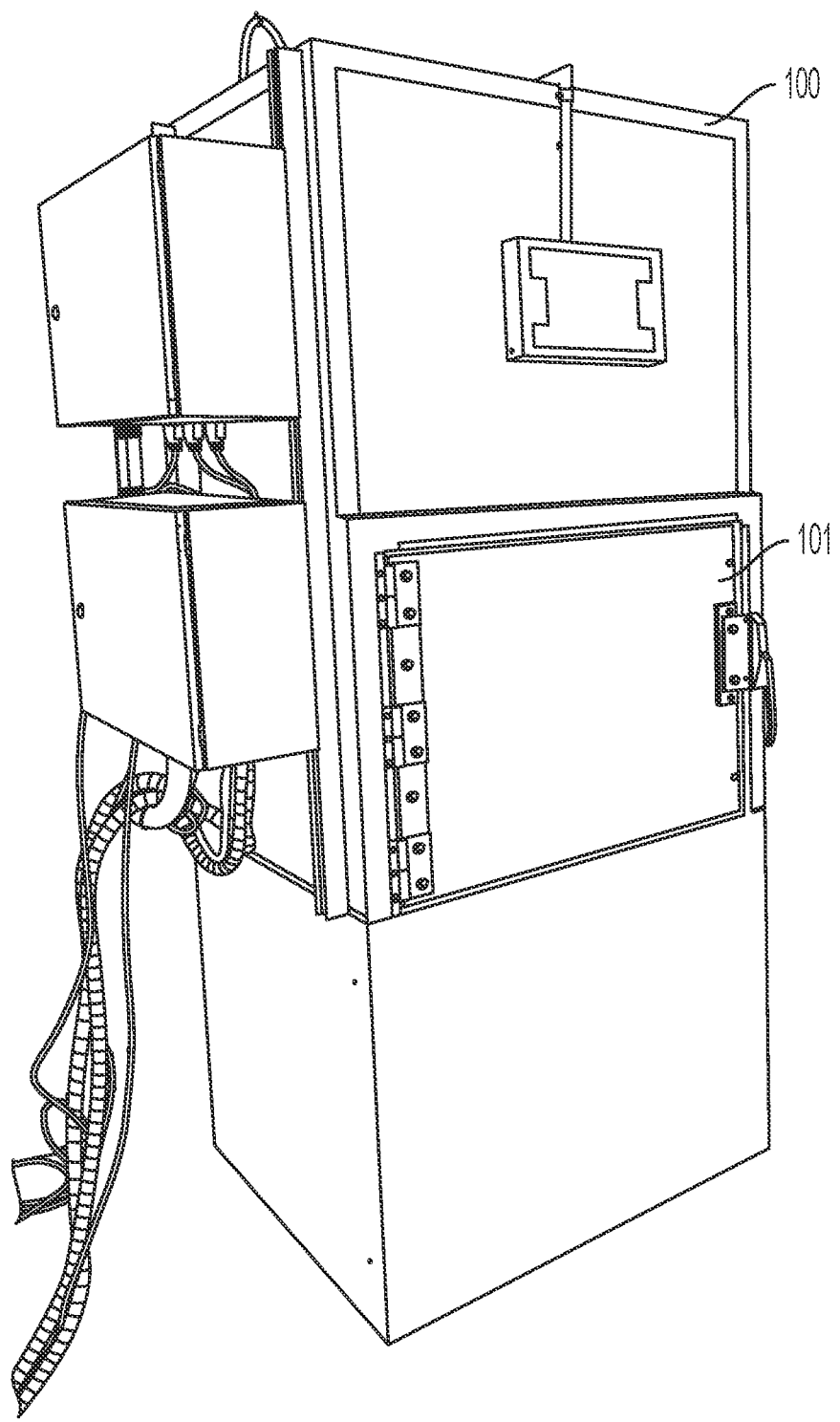
FIG. 2 shows a cabinet of the irradiation system according to an embodiment of the present application.
Figure 3A:
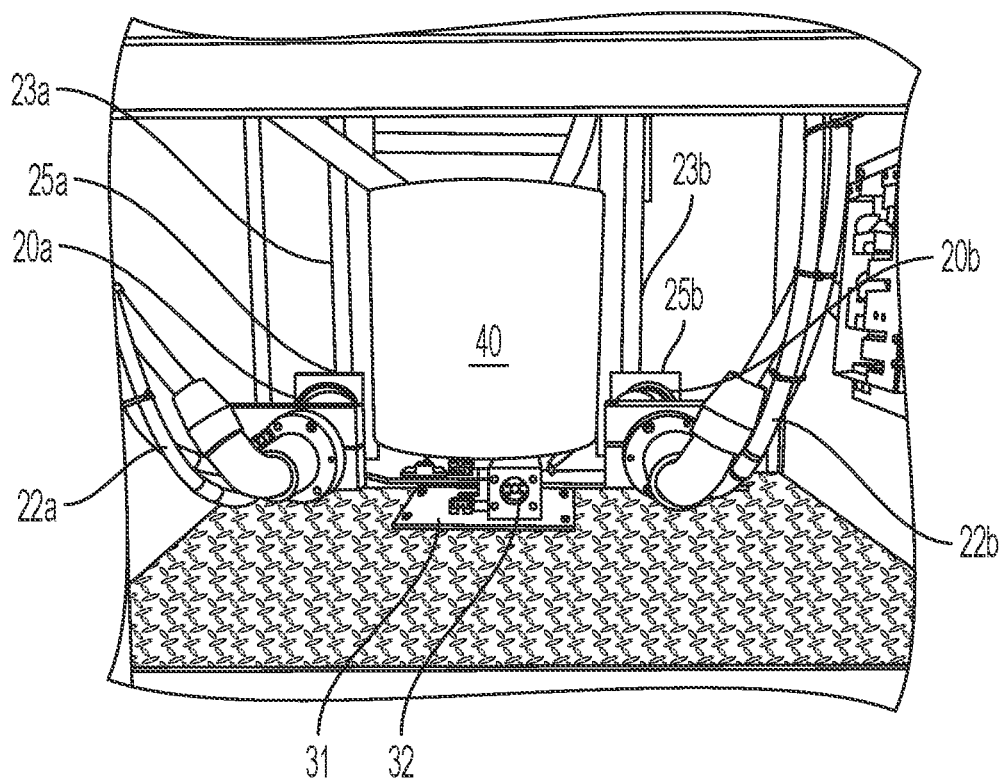
FIGS. 3A-3B show views of an irradiation system according to an embodiment of the present application within a cabinet and including a canister.
Figure 3B:
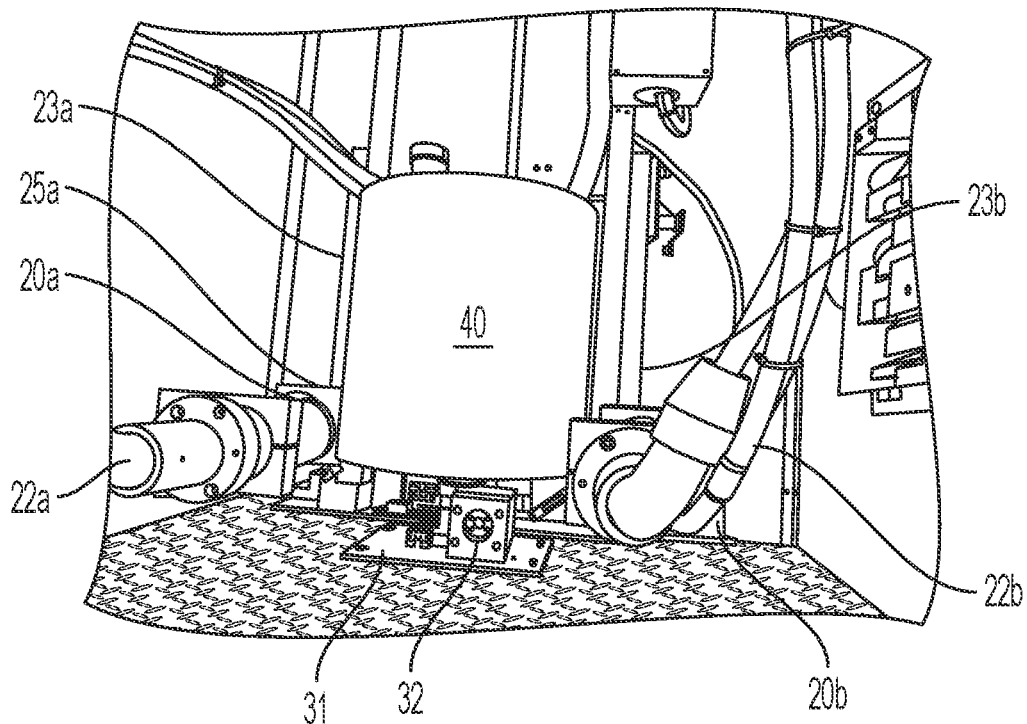
Figure 4A:
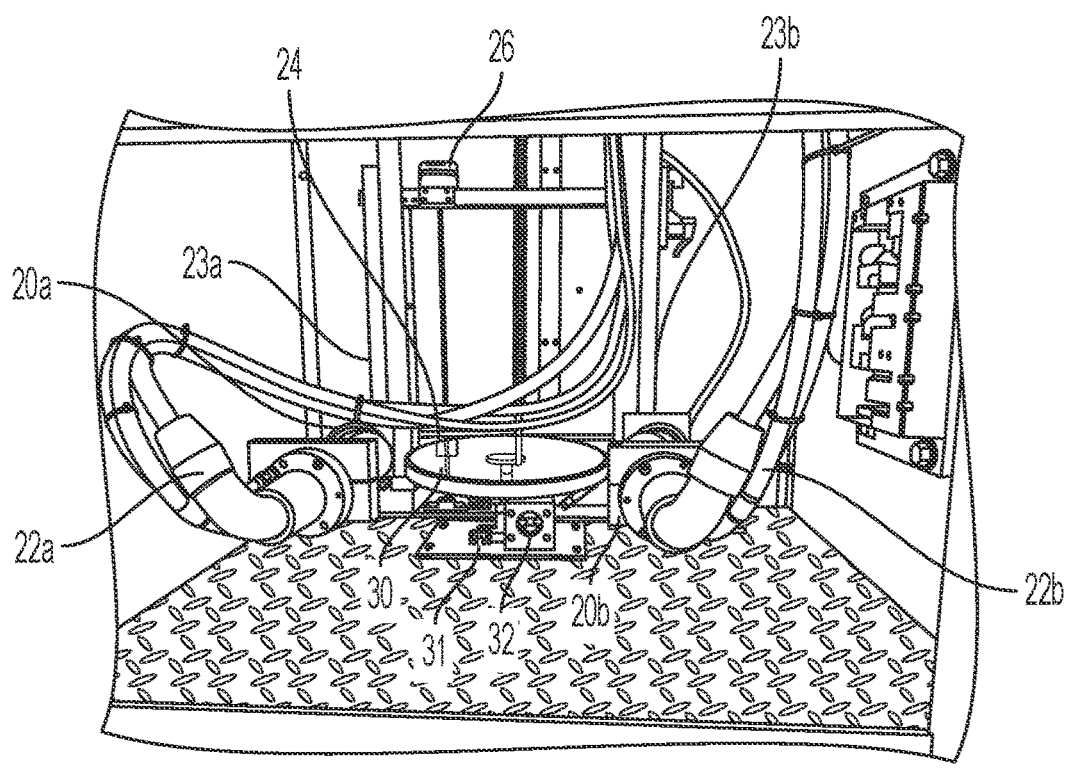
FIGS. 4A-4C show views of an irradiation system according to an embodiment of the present application within a cabinet.
Figure 4B:
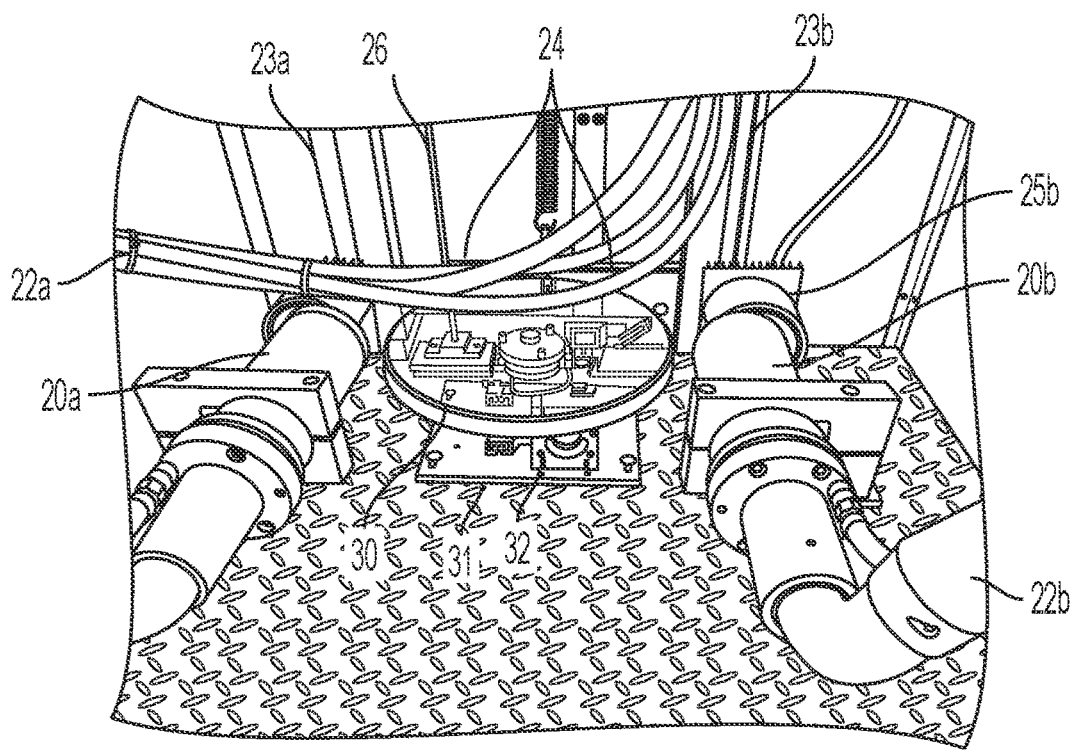
Figure 4C:
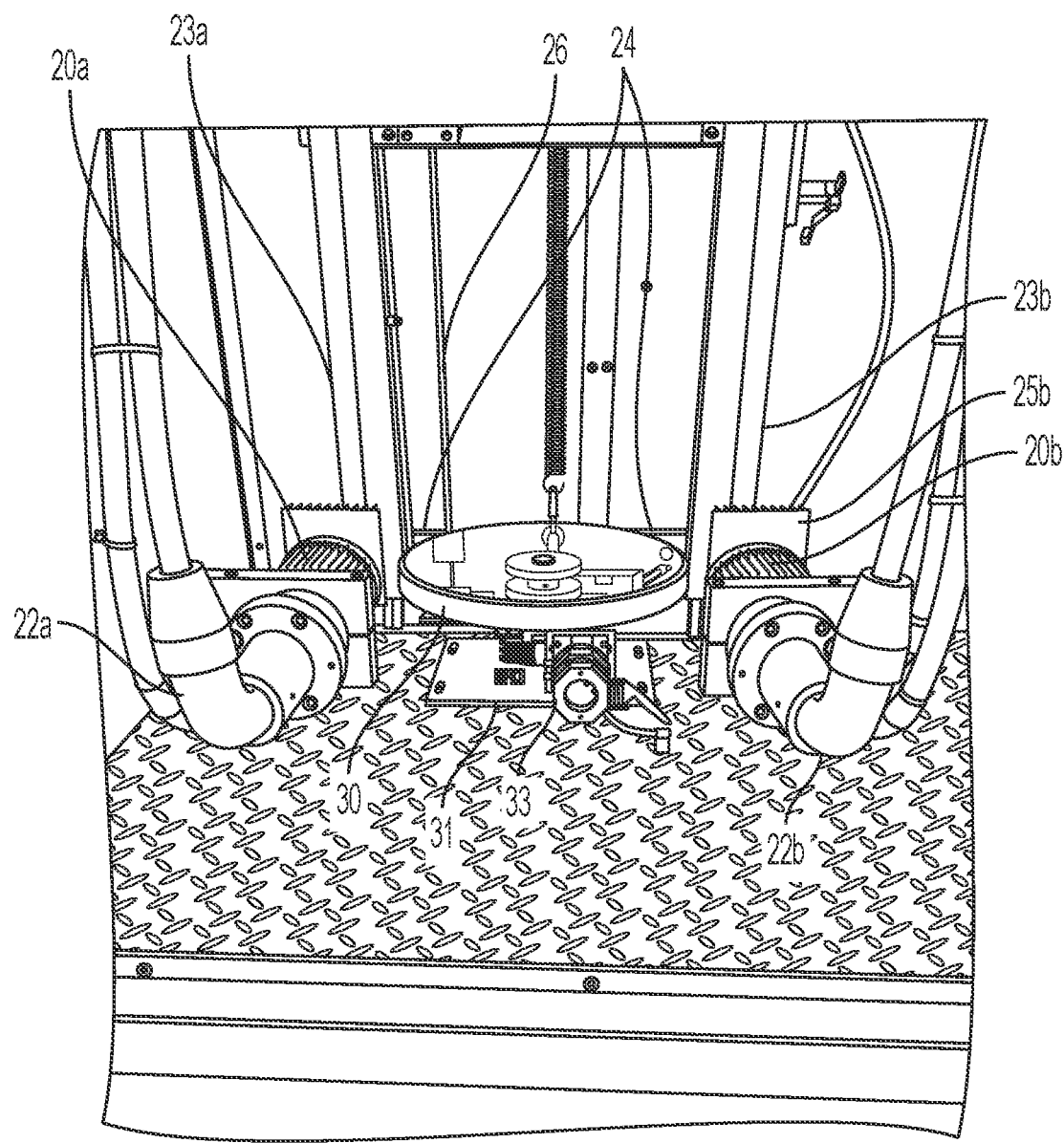

As illustrated in FIG. 1B, rotating the biomass 41 allows for the center of the biomass 41 to constantly receive the conical X-ray beams 21a, 21b during the irradiation process, while the outer portions of the biomass 41 receive the conical X-ray beam 21a, 21b less frequently (i.e., the further from the center the biomass 41 is, the less often it is exposed to the X-rays 21a, 21b). However, because the X-rays 21a, 21b have greater intensity closer to the X-ray tubes 20a, 20b, the radiation is weakest at the center of the biomass 41 receiving the radiation for the longest time duration, and strongest at the perimeter of the biomass 41 receiving the radiation for the shortest time duration. This ensures a more even amount of radiation is provided to the biomass 41 across the cross-sectional area of the biomass 41.

To ensure that the biomass 41 is also evenly irradiated along its vertical height or length, the X-ray tubes 20a, 20b are configured to traverse the vertical axis of the container 40. A linear drive structure 26 can be provided for driving the X-ray tubes 20a, 20b vertically, including for example a pair of vertical tracks 23a, 23b and a horizontal support beam 24. The linear drive 26 may include a lead screw, which can be a threaded rod, and a motor/gearbox that turns the lead screw. The lead screw turns in a threaded hole, which can be drilled in support beam 24. Each of the X-ray tubes 20a, 20b may be provided with a mount 25a, 25b, which may be configured to receive the power cables 22a, 22b therethrough on one end, and to secure the X-ray tubes 20a, 20b to the linear drive structure on the other end, with the X-ray tube 20a, 20b mounted between the two ends. The X-ray tubes 20a, 20b can be secured to either or both of the vertical tracks 23a, 23b or the horizontal beam 24, so that when the linear drive mechanism 26 is activated, the X-ray tubes 20a, 20b move vertically to traverse substantially the entire length of the container 40 and biomass 41. Thus, not only is the biomass 41 radiated evenly across its cross-sectional area, but also evenly along substantially the entire length of the container 40, such that the center of the biomass 41 along the vertical axis is irradiated at the same level as the top and bottom of the biomass 41. The speed of the traversal may vary and can be configured to increase or decrease during the traversal.

Although FIG. 1A shows the X-ray tubes 20a, 20b traversing the container 40 upwardly (i.e., away from the platform 30), the system 10 may be configured for the X-ray tubes 20a, 20b to move downwardly (i.e., from the top of the container 40 towards the platform 30) or in both directions in an alternating manner. The time required for the irradiation process may vary depending on the amount of required dosage, which is a function of the bioburden, in that a greater number of pathogens on a biomass requires a longer irradiation time. The irradiation cycle time according to the present application may range from 45 minutes to 6 hours, depending on the number and intensity of the x-ray tubes being used. The X-ray tubes 20a, 20b can be configured to traverse the container at a linear speed between four inches per hour and thirty inches per hour.

In order to maximize the amount of exposure of the X-ray beams 21a, 21b and reduce wasted energy supplied to the system 10, the X-ray tubes 20a, 20b can be arranged in very close proximity to the container 40, such as near contact between the X-ray tubes 20a, 20b and the container 40. As the X-ray tubes 20a, 20b are arranged closer to the biomass 41, it increases the intensity of the radiation received by the biomass 41 and avoids providing excess radiation to empty space in the cabinet 100. This reduces the amount of time needed for the irradiation process and the power consumption required for the irradiation process. Preferably, the X-ray tubes 20a, 20b are unidirectional, emitting a beam pattern in one direction. The X-ray tubes 20a, 20b may also be wrapped in a corrugated sheet metal heatsink, as shown for example in FIG. 4C, which increases the square inches for cooling.

In certain embodiments of the system 10, the X-ray tubes 20a, 20b are 160 kV and 6 kW X-ray tubes. In other embodiments, X-ray tubes of different wattages or voltages may be used, such as an 8 kW-12 kW tube or a 225 kV tube. Dosage, which is a significant factor to killing pathogens, is a function of power (wattage). In other words, a 160 kV, 12 kW x-ray tube will kill pathogens twice as fast as a 160 kV, 6 kW tube.

In accordance with certain embodiments of the application, during the irradiation process the biomass 41 is placed in a bag, such as a bag of plastic material, which is contained in a cylindrical canister or container 40. In one embodiment, the container 40 may measure approximately twelve inches in diameter, one-eighth inch in thickness and twelve to twenty-four inches in length, depending on the system model. However, the dimensions of the container 40 can vary in other embodiments. The canister or container 40 can be made of any suitable material for housing a biomass 41 while sustaining exposure to X-rays, such as cardboard, paper, or plastic materials. In one embodiment, the container 40 is made of a polymer that presents minimal x-ray beam attenuation while resisting breakdown caused by ionizing radiation.

FIG. 5 illustrates a system 10a and a method for irradiation of contaminants of a biomass in accordance with the present application. The system 10a includes a leaded cabinet 100, within which is provided a rotating platform assembly 30 and an X-ray tube 20a. A lifter system 27 is also provided, which is secured to the rotating platform assembly 30, and is configured to lift and lower the rotating platform assembly 30 relative to the X-ray tube 20a. In the system 10a shown in FIG. 5, the X-ray tube 20a is positioned beneath the rotating platform assembly 30 in the assembly's first, starting position (FIGS. 5A, 5B), but this arrangement may vary in other embodiments, and the X-ray tube 20a may be positioned above or at the same level as the platform assembly 30. The components of the system 10a of FIG. 5 may be similar to those previously described with reference to FIGS. 1-4.

In a first step in a method of using the system 10a to irradiate a biomass, a container 40 is loaded into the leaded cabinet 100 and onto the platform assembly 30 (FIG. 5A). In the figures, the container 40 is cylindrical having a length of twenty-four inches and a diameter of twelve inches and is filled with a biomass, but in other embodiments the dimensions and content of the container 40 may vary. Once loaded onto the platform 30, a power-up cycle begins in a first, "home" position (FIG. 5B). Upon power-up, the remediation process begins, and the platform 30 and container 40 begin to rotate about a central axis along the length of the container 40 and the X-ray tube 20a is turned on (FIG. 5C). The container platform 30 continues to rotate and begins to descend, where the container 40 passes the X-ray tube 20a, exposing the biomass 41 to the X-ray beam 21a (FIGS. 5D, 5E). The platform 30 continues its rotation and descent through the cabinet 100 and past the X-ray tube 20a, such that substantially the entire cylindrical container 40 is exposed to the X-ray beam 21a generated by the X-ray tube 20a (FIG. 5F). As the remediation or exposure cycle comes to an end, the container 40 rotation begins to cease, and the X-ray exposure cycle concludes (FIG. 5G). The rotation of the platform 30 and container 40 stops, and the platform 30 and container 40 ascend back to the initial "home" position (FIG. 5H). Once the platform 30 and container 40 have returned to the "home" position, the irradiation cycle is completed, the container 40 can be removed and replaced with a new container 40 to begin a new cycle (FIG. 5I).

FIG. 6 illustrates a further system 10b and a method for irradiation of contaminants in accordance with the present application. The system 10b includes a leaded cabinet 100, within which is provided a rotating platform assembly 30 and two opposing X-ray tubes 20a, 20b. The system 10b in FIG. 6 is similar to that shown in FIG. 5, except that a second X-ray tube 20b is provided opposite the first X-ray tube 20a. A lifter system 27 is also provided, which is secured to the rotating platform assembly 30, and is configured to lift and lower the rotating platform assembly 30 relative to the X-ray tubes 20a, 20b. In the system arranged in FIG. 6, the X-ray tubes 20a, 20b are positioned beneath the rotating platform assembly 30 in its starting position, but this arrangement may vary in other embodiments, and the X-ray tubes 20a, 20b may be positioned above or at the same level as the platform assembly 30. The components of the system 10b of FIG. 6 may be similar to those previously described with reference to FIGS. 1-4.

In a first step in a method of using the system 10b to irradiate a biomass, a container 40 is loaded into the leaded cabinet 100 and onto the platform assembly 30 (FIG. 6A). In the figures, the container 40 is cylindrical having a length of twenty-four inches and a diameter of twelve inches and is filled with a biomass, but in other embodiments the dimensions and content of the container 40 may vary. Once loaded onto the platform 30, a power-up cycle begins in a first, "home" position (FIG. 6B). Upon power-up, the remediation process begins, and the container 40 begins to rotate about a central axis along the length of the container 40 and the X-ray tubes 20a, 20b are turned on (FIG. 6C). The container platform 30 continues to rotate and begins to descend, where the container 40 passes the X-ray tubes 20a, 20b, exposing the biomass 41 in the container 40 to the X-ray beams 21a, 21b generated by the X-ray tubes 20a, 20b (FIGS. 6D, 6E). The platform 30 continues its rotation and descent through the cabinet 100 and past the X-ray tubes 20a, 20b, such that substantially the entire cylindrical container 40 is exposed to the X-ray tubes 20a, 20b (FIG. 6F). As the remediation or exposure cycle comes to an end, the container 40 rotation begins to cease, and the X-ray exposure cycle concludes (FIG. 6G). The rotation of the platform 30 and container 40 stops, and the platform 30 and container 40 ascend back to the initial "home" position (FIG. 6H). Once the platform 30 and container 40 have returned to the "home" position, the irradiation cycle is completed, the container 40 can be removed and replaced with a new container 40 to begin a new cycle (FIG. 6I).

FIG. 7 illustrates a further system 10c and a method for irradiation of contaminants in accordance with the present application. The system 10c includes a leaded cabinet 100, within which is provided a rotating platform assembly 30 and two opposing X-ray tubes 20a, 20b. A lifter system, including vertical tracks 23a, 23b, support beam 24, and linear drive 26, is also provided, which is secured to the X-ray tubes 20a, 20b, and is configured to lift and lower the X-ray tubes 20a, 20b relative to the rotating platform assembly 30. The system 10c in FIG. 7 is similar to that shown in FIG. 6, except that in the system of FIG. 6, the platform assembly 30 is static, and the X-ray tubes 20a, 20b are raised and lowered. The system 10c shown in FIG. 7 is similar to that shown and described in FIGS. 1-4. In the system 10c in FIG. 7, the X-ray tubes 20a, 20b are positioned adjacent to and substantially level with the rotating platform assembly 30 in the first, starting position of the X-ray tubes 20a, 20b, but this arrangement may vary in other embodiments, and the X-ray tubes 20a, 20b may be positioned above or below the platform assembly 30 as their starting position. The components of the system 10c of FIG. 7 may be similar to those previously described with reference to FIGS. 1-4.

In a first step in a method of using the system 10c to irradiate a biomass, a container 40 is loaded into the leaded cabinet 100 and onto the platform assembly 30 (FIG. 7A). In the figures, the container 40 is cylindrical having a length of twenty-four inches and a diameter of twelve inches and is filled with a biomass 41, but in other embodiments the dimensions and content of the container 40 may vary. Once the container 40 is loaded onto the platform 30, a power-up cycle begins in a first, "home" position (FIG. 7B). Upon power-up, the remediation process begins, and the platform 30 and container 40 begin to rotate about a central axis along the length of the container 40 and the X-ray tubes 20a, 20b are turned on (FIG. 7C). The container platform 30 continues to rotate, and the X-ray tubes 20a, 20b begin to ascend, where the X-ray tubes 20a, 20b pass the container 40, exposing the biomass 41 in the container 40 to the X-ray beams 21a, 21b generated by the X-ray tubes 20a, 20b (FIGS. 7D, 7E). The platform 30 continues its rotation, and the X-ray tubes 20a, 20b continue ascending through the cabinet 100 and past the container 40, such that substantially the entire cylindrical container 40 is exposed to the X-ray tubes 20a, 20b (FIG. 7F). As the remediation or exposure cycle comes to an end, the container 40 rotation begins to cease, and the X-ray exposure cycle concludes (FIG. 7G). The rotation of the platform 30 and container 40 stops, and the X-ray tubes 20a, 20b descend back to the initial "home" position (FIG. 7H). Once the X-ray tubes 20a, 20b and lift have returned to the "home" position, the irradiation cycle is completed, the container 40 can be removed and replaced with a new container 40 to begin a new cycle (FIG. 6I).

In embodiments in which a biomass to be irradiated can be damaged at high temperatures, additional modifications can be made to the system. For example, if *cannabis* is to be irradiated, if exposed to temperatures above around 80° F., the *cannabis* can suffer terpene loss, which is undesirable. Because x-ray tubes generate heat during operation despite being liquid cooled, it is possible for the interior of the leaded cabinet to get above the 80-degree threshold (or another threshold temperature) whilst the flower is being remediated. To counter this, a thermal probe can be installed inside the cabinet and monitors the interior temperature during the remediation process. A pagoda-style air conditioning unit, or other cooling unit, can also be mounted to the top of the cabinet and configured to turn on (via a command by the system's PLC) if the interior of the cabinet reaches a preset temperature threshold. The air conditioning unit can be configured to cycle off once the temperature inside the cabinet reaches the lower threshold.

In addition, constant potential x-ray emitters/tubes have a tendency to arc on occasion, a phenomenon that occurs when enough impurities from out-gassing materials allow temporary conductivity across the cathode to anode (or anode to cathode) vacuum. This event has the potential to damage either the high voltage power supply, the high voltage cable, or the x-ray emitter/tube itself. As a result, typically the high voltage power supply will shut down to protect itself. In other applications, such as x-ray imaging biological irradiation, the disruption can be problematic and often requires the retake of an image or the repeat of a scientific experiment.

Remediation of some products, such as *cannabis*, may only require a coarse operation and does not require such a precise application of dose. As such, in certain embodiments, the high voltage power supply can be configured to ignore up to three emitter/tube arcs occurring within a preset amount of time (such as 1-3 seconds) so that the remediation operation is not interrupted, hampering throughput, and requiring a re-start to be initiated by the operator. Moreover, the high voltage power supply used in the present application comprises a very robust surge resistor such that emitter/tube arcs will not cause damage.

While there have been shown and described and pointed out fundamental novel features of the irradiation device, system and method as applied to embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice.

What is claimed:

1. A sterilization method comprising:
axially rotating a container, comprising therein contents to be sterilized, on a platform;
generating an X-ray beam by at least one X-ray tube, the X-ray beam being directed towards the container; and
moving the platform or the at least one X-ray tube concurrent with axial rotation of the container so that substantially an entire length of the container is traversed by the X-ray beam.

2. The method according to claim 1, wherein points on a perimeter of the container receive a higher level of radiation from the X-ray beam than a center of the container and are exposed to the X-ray beam for a shorter duration of time than the center of the container.

3. The method according to claim 1, wherein the container is cylindrical.

4. The method according to claim 3, wherein the generating the X-ray beam by the at least one X-ray tube comprises emitting the X-ray beam in a directional beam pattern in a single direction toward the container.

5. The method according to claim 4, wherein the at least one X-ray tube is arranged in near surface contact with the container, and the X-ray beam does not encompass the width of the container on an outer portion of the container.

6. The method according to claim 1, wherein a traversal speed of the platform or a traversal speed of the at least one X-ray tube is reduced at a leading edge of the container.

7. The method according to claim 1, wherein the at least one X-ray tube comprises two X-ray tubes arranged on opposite sides of the container, and the method further comprises:
generating the X-ray beams by the two X-ray tubes, the X-ray beams contacting opposing sides of the rotating container.

8. The method according to claim 7, further comprising:
traversing the length of the container a first time by the two X-ray tubes by moving the two X-ray tubes along the length of the container in a first direction concurrent with the axial rotation of the platform; and
traversing the length of the container a second time by the two X-ray tubes by moving the two X-ray tubes along the length of the container in a second direction opposite the first direction concurrent with the axial rotation of the platform.

9. The method according to claim 1, further comprising:
traversing the length of the container a first time by the at least one X-ray tube by moving the at least one X-ray tube along the length of the container in a first direction concurrent with the axial rotation of the platform; and
traversing the length of the container a second time by the at least one X-ray tube by moving the at least one X-ray tube along the length of the container in a second direction opposite the first direction concurrent with the axial rotation of the platform.

10. The method according to claim 1, further comprising:
traversing the length of the container a first time by the at least one X-ray tube by moving the platform in a first direction concurrent with the axial rotation of the platform; and
traversing the length of the container a second time by the at least one X-ray tube by moving the platform in a second direction opposite the first direction concurrent with the axial rotation of the platform.

11. A method for sterilization of a biomass comprising:
loading a container stored with a biomass to be sterilized onto a platform in a sterilization apparatus, the platform being configured for axial rotation; and
performing a sterilization process configured to sterilize the biomass in the container with at least one X-ray tube of the sterilization apparatus configured to generate an X-ray beam directed towards the container;
wherein the sterilization process comprises concurrently:
rotating the container on the platform,
generating the X-ray beam by the at least one X-ray tube and directing the X-ray beam towards the container, and
traversing a length of the container with the at least one X-ray tube concurrent with the axial rotation of the platform so that over the sterilization process, substantially an entire length of the container is exposed to the X-ray beam.

12. The method according to claim 11, wherein points on a perimeter of the container receive a higher level of radiation from the X-ray beam than a center of the container and are exposed to the X-ray beam for a shorter duration of time than the center of the container.

13. The method according to claim 11, wherein the container is cylindrical.

14. The method according to claim 11, wherein the generating the X-ray beam by the at least one X-ray tube comprises emitting the X-ray beam in a directional beam pattern in a single direction toward the container.

15. The method according to claim 14, wherein the at least one X-ray tube is arranged in near surface contact with the container, and the X-ray beam does not encompass the width of the container on an outer portion of the container.

16. The method according to claim 11, wherein a traversal speed of the at least one X-ray tube is reduced at a leading edge of the container.

17. The method according to claim 11, wherein the rotating the container on the platform comprises rotating the container 360° at a rotation speed between five to ten revolutions per minute.

18. The method according to claim 11, wherein a rate of the traversing of the container with the at least one X-ray tube is between four inches per hour and thirty inches per hour.

19. The method according to claim 11, wherein the container comprises a diameter of approximately twelve inches and a length between twelve to twenty-four inches.

20. The method according to claim 11, wherein the at least one X-ray tube comprises two X-ray tubes arranged on opposite sides of the container, and the method further comprises:
generating the X-ray beams by the two X-ray tubes, the X-ray beams contacting opposing sides of the rotating container.

21. The method according to claim 20, wherein the traversing the length of the container with the at least one X-ray tube comprises:
traversing the length of the container a first time by the two X-ray tubes by moving the two X-ray tubes along the length of the container in a first direction concurrent with the axial rotation of the platform; and
traversing the length of the container a second time by the two X-ray tubes by moving the two X-ray tubes along the length of the container in a second direction opposite the first direction concurrent with the axial rotation of the platform.

22. The method according to claim 11, wherein the traversing a length of the container with the at least one X-ray tube comprises:
traversing the length of the container a first time by the at least one X-ray tube by moving the at least one X-ray tube along the length of the container in a first direction concurrent with the axial rotation of the platform; and
traversing the length of the container a second time by the at least one X-ray tube by moving the at least one X-ray tube along the length of the container in a second direction opposite the first direction concurrent with the axial rotation of the platform.

23. The method according to claim 11, wherein the traversing a length of the container with the at least one X-ray tube comprises:
traversing the length of the container a first time by the at least one X-ray tube by moving the platform in a first direction concurrent with the axial rotation of the platform; and
traversing the length of the container a second time by the at least one X-ray tube by moving the platform in a second direction opposite the first direction concurrent with the axial rotation of the platform.

* * * * *